US010337008B2

(12) United States Patent
Terzi et al.

(10) Patent No.: US 10,337,008 B2
(45) Date of Patent: Jul. 2, 2019

(54) METHODS FOR PREDICTING THE PROGRESSION AND TREATING A CHRONIC KIDNEY DISEASE IN A PATIENT

(71) Applicants: Fabiola Terzi, Paris (FR); Amandine Viau, Paris (FR); Clément Nguyen, Paris (FR); Martine Burtin, Paris (FR); Khalil El Karoui, Paris (FR)

(72) Inventors: Fabiola Terzi, Paris (FR); Amandine Viau, Paris (FR); Clément Nguyen, Paris (FR); Martine Burtin, Paris (FR); Khalil El Karoui, Paris (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 213 days.

(21) Appl. No.: 15/152,604

(22) Filed: May 12, 2016

(65) Prior Publication Data

US 2016/0244764 A1 Aug. 25, 2016

Related U.S. Application Data

(63) Continuation of application No. 13/876,859, filed as application No. PCT/EP2011/067236 on Oct. 3, 2011, now abandoned.

(30) Foreign Application Priority Data

Oct. 1, 2010 (EP) .................................... 10306077

(51) Int. Cl.
| | |
|---|---|
| *C12N 15/11* | (2006.01) |
| *C12N 15/113* | (2010.01) |
| *C12Q 1/6883* | (2018.01) |
| *G01N 33/68* | (2006.01) |
| *A61K 9/00* | (2006.01) |
| *C07K 16/28* | (2006.01) |

(52) U.S. Cl.
CPC ........ *C12N 15/1135* (2013.01); *A61K 9/0019* (2013.01); *C07K 16/2803* (2013.01); *C12Q 1/6883* (2013.01); *G01N 33/6893* (2013.01); C07K 2317/76 (2013.01); C12N 2310/122 (2013.01); C12N 2310/14 (2013.01); C12N 2310/16 (2013.01); C12N 2310/531 (2013.01); C12Q 2600/118 (2013.01); G01N 2800/347 (2013.01); G01N 2800/56 (2013.01)

(58) Field of Classification Search
None
See application file for complete search history.

(56) References Cited

U.S. PATENT DOCUMENTS

2005/0261191 A1* 11/2005 Barasch ............. A61K 38/1709
514/15.1

FOREIGN PATENT DOCUMENTS

| WO | 2005/107793 A2 | 11/2005 |
| WO | 2008/049330 A1 | 5/2008 |
| WO | 2009/114699 A2 | 9/2009 |
| WO | 2009/132510 A1 | 11/2009 |
| WO | 2010/042997 A1 | 4/2010 |

OTHER PUBLICATIONS

Bolignano et al., "Neutrophil gelatinase-associated lipocalin reflects the severity of renal impairment in subjects affected by chronic kidney disease", Kidney and Blood Pressure Research, Sep. 1, 2008, pp. 255-258, vol. 31, No. 4, CH.
Bolignano et al., "Neutrophil gelatinase-associated lipocalin (NGAL) and Progression of Chronic Kidney Disease", Clinical Journal of The American Society of Nephrology, Feb. 1, 2009, pp. 337-344 vol. 4, No. 2.
Ko et al., "Transcriptional analysis of kidneys during repair from AKI reveals possible roles for NGAL and KIM-1 as biomarkers of AKI-to-CKD transition", AJP: Renal Physiology, Jun. 1, 2010, pp. F1472-F1483, vol. 298, No. 6.
Vinuesa et al., "Lipocalin-2-induced renal regeneration depends on cytokines", AJP: Renal Physiology, Nov. 1, 2008, pp. F1554-F1562, vol. 295, No. 5.
Viau et al., "Lipocalin 2 is essential for chronic kidney disease progression in mice and humans", The Journal of Clinical Investigation, Nov. 1, 2010, pp. 4065-4076, vol. 120, No. 11.
Eisner-Dorman et al. Brain, Behav. Immun. 2009; 23:318-324.
Elsea and Lucas, R.E. Ilar J. 2002; 43(2):66-79.
Kumar et al., Genesis 2004; 38:51-57.
Mishra et al., J. Am. Soc. Nephrol. 2004; 15:3073-3082.
Vinuesa et al., Am. J. Physiol. Renal Physiol. 2008; 295:F1554-F1562.

\* cited by examiner

*Primary Examiner* — Ekaterina Poliakova-Georgantas
(74) *Attorney, Agent, or Firm* — W&C IP

(57) ABSTRACT

The present invention relates to a method for predicting the progression of chronic kidney disease (CKD) in a patient and also to an inhibitor of NGAL gene expression or an NGAL antagonist for use in the prevention or the treatment of CKD.

5 Claims, No Drawings

Specification includes a Sequence Listing.

SEQUENCE LISTING

<160> NUMBER OF SEQ ID NOS: 4

<210> SEQ ID NO 1
<211> LENGTH: 19
<212> TYPE: DNA
<213> ORGANISM: Artificial
<220> FEATURE:
<223> OTHER INFORMATION: Synthetic Lcn2 shRNA sequence

<400> SEQUENCE: 1
ggaaatatgc acaggtatc                                                19

<210> SEQ ID NO 2
<211> LENGTH: 19
<212> TYPE: DNA

```
<213> ORGANISM: Artificial
<220> FEATURE:
<223> OTHER INFORMATION: Synthetic Lcn2 shRNA sequence

<400> SEQUENCE: 2
gctactggat cagaacatt                                               19

<210> SEQ ID NO 3
<211> LENGTH: 19
<212> TYPE: DNA
<213> ORGANISM: Artificial
<220> FEATURE:
<223> OTHER INFORMATION: Synthetic shRNA scramble sequence

<400> SEQUENCE: 3
gagcgtacca gattaaagt                                               19

<210> SEQ ID NO 4
<211> LENGTH: 19
<212> TYPE: DNA
<213> ORGANISM: Artificial
<220> FEATURE:
<223> OTHER INFORMATION: Synthetic shRNA scramble sequence

<400> SEQUENCE: 4
gattcgacca gacatgtat                                               19
```

US 10,337,008 B2

METHODS FOR PREDICTING THE PROGRESSION AND TREATING A CHRONIC KIDNEY DISEASE IN A PATIENT

FIELD OF THE INVENTION

The present invention relates to a method for predicting the progression of chronic kidney disease (CKD) in a patient and also to an inhibitor of NGAL gene expression or an NGAL antagonist for use in the prevention or the treatment of CKD.

BACKGROUND OF THE INVENTION

Regardless of the initial insult, human chronic kidney disease (CKD) is characterized by progressive destruction of the renal parenchyma and the loss of functional nephrons which ultimately lead to end stage renal failure (ESRF). CKD represents a worldwide concern: in the USA, 102,567 patients began dialysis in 2003 (341 patients/year per/million) (1), and similar rates were found in developing countries and in particular ethnic groups (2). However, these numbers are a small fraction of the millions of patients who are thought to have some degree of renal impairment. In the United States the prevalence of chronically reduced kidney function is 11% of adults (3). Understanding the pathophysiology of CKD progression is, therefore, a key challenge for medical planning.

The mechanisms of CKD progression are poorly understood. It has been shown that reduction of the number of functional nephrons triggers molecular and cellular events promoting compensatory growth of the remaining ones (4). In some cases, this compensatory process becomes pathological with the development of renal lesions and ESRF. Although the pathophysiology of compensation and progression is complex, unregulated proliferation of glomerular, tubular and interstitial cells may promote the development of glomerulosclerosis, tubular cysts, and interstitial fibrosis (5-7). The molecular programs that control this cascade of events are largely unknown.

Attempts to dissect the molecular basis of CKD have been facilitated by the development of several experimental models of renal deterioration. Among these, the remnant kidney model is a mainstay, since nephron reduction characterizes the evolution of most human CKD. Consequently, this model recapitulates many features of human CKD, including hypertension, proteinuria, glomerular and tubulointerstitial lesions. Over the last fifty years, this model has led to the discovery of critical pathways and, more importantly, to the design of therapeutic strategies to slow down the progression of CKD, such as the widely clinically used renin-angiotensin inhibitors (8).

More recently, studies in different mouse strains have highlighted the importance of genetic factors in the evolution of experimental nephron reduction (9-11). We previously showed that the course and extent of renal lesions following nephron reduction vary significantly between two mouse strains: whereas the FVB/N mice develop severe lesions, the (C57BL/6xDBA2)F1 (hereafter denoted B6D2F1) undergoes compensation alone (12). Moreover, we observed that the development of renal lesions paralleled the extent of cell proliferation (12). In fact, once the compensatory growth is achieved, a second wave of cell proliferation occurs only in the FVB/N strain.

There is a need in the art for a reliable biomarker which allows the prediction of the progression of CKD in particular in human patients suffering from said disease as well as relevant treatments for preventing or treating CKD.

SUMMARY OF THE INVENTION

The present invention thus relates to a method for predicting the progression of chronic kidney disease (CKD) or for monitoring CKD therapy in a patient, comprising the following steps:
a. providing a biological sample from said patient suffering from CKD,
b. determining the expression level of Neutrophil Gelatinase-Associated Lipocalin (NGAL) gene, and
c. correlating the expression level of NGAL gene with the prediction of the progression of CKD.

The present invention also relates to an inhibitor of NGAL gene expression for use in the prevention or the treatment of CKD.

The present invention further relates to an NGAL antagonist for use in the prevention or the treatment of CKD.

DETAILED DESCRIPTION OF THE INVENTION

Definitions

Throughout the specification, several terms are employed and are defined in the following paragraphs.

As used herein, the terms "Lipocalin 2" (Lcn2) or "NGAL" have their general meaning in the art and refer to the Neutrophil Gelatinase-Associated Lipocalin as described in Schmidt-Ott K M. et al. (2007). NGAL can be from any source, but typically is a mammalian (e.g., human and non-human primate) NGAL, particularly a human NGAL. The term "NGAL gene" refers to any nucleotide sequence encoding the NGAL mRNA and protein, such as a genomic DNA sequence and any naturally occurring NGAL and variants and modified forms thereof. It can also encompass artificial sequences such as cDNA encoding the NGAL mRNA and protein. An exemplary human native NGAL nucleotide sequence is provided in GenBank database under accession number NM_005564. The term "NGAL mRNA" has its general meaning in the art and refers to the messenger RNA which is synthesized upon expression of the NGAL gene. The term "NGAL protein" refers to the amino acid sequence resulting from the expression of the NGAL gene, and any naturally occurring NGAL and variants and modified forms thereof. An exemplary human native NGAL amino acid sequence is provided in GenPept database under accession number NP_005555. NGAL is a glycoprotein and was originally identified as a neutrophil specific granule component and a member of the lipocalin family of proteins. The protein was shown to exist both as a 25-kDa monomer and a 45-kDa disulfide-linked homodimer, and it may also be covalently complexed with neutrophil gelatinase (also known as matrix metalloproteinase 9, MMP-9) via an intermolecular disulphide bridge as a 135-kDa heterodimeric form.

An "inhibitor of gene expression" refers to a natural or synthetic compound that has a biological effect to inhibit or significantly reduce the expression of a gene. Thus, an "inhibitor of NGAL gene expression" refers to a natural or synthetic compound that has a biological effect to inhibit or significantly reduce the expression of the gene encoding for NGAL.

The term "NGAL antagonist" refers to a compound, natural or not, which has the capability to inhibit (partly or totally) the biological activity of the NGAL protein. The scope of the present invention includes all those NGAL antagonists now known and those NGAL antagonists to be discovered in the future. This term includes anti-NGAL antibody.

The term "anti-NGAL antibody" refers to an antibody or a fragment thereof which recognizes NGAL.

The term "chronic kidney disease" (CKD) has its general meaning in the art and is used to classify numerous conditions that affect the kidney, destruction of the renal parenchyma and the loss of functional nephrons. CKD include polycystic kidney disease (Autosomal Dominant Polycystic Kidney Disease (ADPKD) and Autosomal Recessive Polycystic Kidney Disease (ARPKD), glomerulonephritis, interstitial nephritis, nephropathy and obstructive uropathy.

As used herein, the term "predetermined value" refers to the amount of NGAL in biological samples obtained from the general population or from a selected population of subjects. For example, the selected population may be comprised of apparently healthy subjects, such as individuals who have not previously had any sign or symptoms indicating the presence of chronic kidney disease (CKD). In another example, the predetermined value may be of the amount of NGAL obtained from subjects having an established CKD. The predetermined value can be a threshold value, or a range. The predetermined value can be established based upon comparative measurements between apparently healthy subjects and subjects with established CKD.

As used herein, the term "patient" denotes a mammal, such as a rodent, a feline, a canine, and a primate. Preferably, a patient according to the invention is a human.

Predictive Methods of the Invention

The present invention relates to a method for predicting the progression of chronic kidney disease (CKD) or for monitoring CKD therapy in a patient,
comprising the following steps:
a. providing a biological sample from said patient suffering from CKD,
b. determining the expression level of Neutrophil Gelatinase-Associated Lipocalin (NGAL) gene, and
c. correlating the expression level of NGAL gene with the prediction of the progression of CKD.

In one embodiment, the present invention relates to a method for predicting the progression of chronic kidney disease (CKD) or for monitoring CKD therapy in a patient comprising determining the quantity of mRNA encoding NGAL in a cell or tissue sample obtained from said patient.

In a particular embodiment, the tissue sample is a kidney biopsy.

Determination of the expression level of a gene can be performed by a variety of techniques. Generally, the expression level as determined is a relative expression level.

More preferably, the determination comprises contacting the sample with selective reagents such as probes, primers or ligands, and thereby detecting the presence, or measuring the amount of nucleic acids of interest originally in the sample.

In a preferred embodiment, the expression level may be determined by determining the quantity of mRNA.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). In a preferred embodiment, the expression level of the NGAL gene is determined by RT-PCR, preferably quantitative or semi-quantitative RT-PCR, even more preferably real-time quantitative or semi-quantitative RT-PCR.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In another embodiment, the present invention relates to a method for predicting the progression of CKD or for monitoring CKD therapy in a patient comprising measuring the concentration of NGAL protein in a biological sample obtained from said patient.

In a particular embodiment, the concentration of the NGAL protein is measured in a blood sample, a plasma sample, a serum sample or a urine sample obtained from said patient.

In still another embodiment, the methods of the invention comprise contacting the biological sample with a binding partner capable of selectively interacting with the NGAL protein present in the biological sample. The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce anti-NGAL, single chain antibodies. Antibodies useful in practicing the present invention also include anti-NGAL fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to NGAL. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

Monoclonal antibodies for NGAL are described, for example, in Kjeldsen et al., (1996). Examples of commercially available monoclonal antibodies for NGAL include those obtained from the Antibody Shop, Copenhagen, Denmark, as HYB-211-01, HYB-211-02, and NYB-211-05. Typically, HYB-211-01 and HYB-211-02 can be used with NGAL in both its reduced and unreduced forms. NGAL antibodies can also be purchased from R&D Systems under reference AF1857.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S.D., 1999. Peptide aptamers consist of conformationally constrained antibody variable regions displayed by a platform protein, such as E. coli Thioredoxin A, that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays generally involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The concentration of the NGAL protein may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

In a particular embodiment, the concentration of the NGAL protein is measured by immunoassay.

More particularly, an ELISA method can be used, wherein the wells of a microtiter plate are coated with a set of anti-NGAL antibodies. A biological sample containing or suspected of containing NGAL is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Suitable ELISA methods for the detection of NGAL were described in Kjeldsen et al. (1996), Mishra J. et al. (2005) and Wang et al. (2007). A sandwich enzyme immunoassay for the detection of NGAL was described by B laser J. et al. (1995). A radioimmunoassay for the detection of NGAL was described by Xu S Y. et al (1994).

ELISA kits for detecting NGAL are commercially available from AntibodyShop (Grusbakken 8 DK-2820 Gentofte—Denmark) under the reference KIT 036 or KIT 037, from R&D Systems Europe (Lille—France) under the reference DLCN20 and from MBL International, Wobum, Mass. 01801, USA) under reference CY-8070.

Measuring the concentration of the NGAL protein (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, NGAL may be identified based on the known "separation profile" e. g., retention time, for that compound and measured using standard techniques.

Alternatively, the separated compounds may be detected and measured by, for example, a mass spectrometer.

In one embodiment, the method of the invention further may comprise a step of comparing the concentration of the NGAL protein with a predetermined threshold value. Said comparison is indicative of the progression of CKD in the patient or the responsiveness of the patient to the treatment against CKD.

Therapeutic Methods and Uses

The invention provides methods and compositions (e.g. pharmaceutical compositions) for use in the prevention or the treatment of chronic kidney disease (CKD) in a patient.

Accordingly, in one aspect the present invention relates to an inhibitor of NGAL gene expression for use in the prevention or the treatment of CKD.

Inhibitors of NGAL gene expression for use in the present invention may be based on anti-sense oligonucleotide constructs. Anti-sense oligonucleotides, including anti-sense RNA molecules and anti-sense DNA molecules, would act to directly block the translation of NGAL mRNA by binding thereto and thus preventing protein translation or increasing mRNA degradation, thus decreasing the level of NGAL, and thus activity, in a cell. For example, antisense oligonucleotides of at least about 15 bases and complementary to unique regions of the mRNA transcript sequence encoding NGAL can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) may also function as inhibitors of NGAL gene expression for use in the present invention. NGAL gene expression can be reduced by contacting a subject or cell with a small double stranded RNA (dsRNA), or a vector or construct causing the production of a small double stranded RNA, such that NGAL gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). Short hairpin RNA (shRNA) may also function as inhibitors of NGAL gene expression for use in the present invention.

In one embodiment, the sequence of the shRNA targeting NGAL (Lcn2) is represented by SEQ ID NO: 1.

In another embodiment, the sequence of the shRNA targeting NGAL (Lcn2) is represented by SEQ ID NO: 2.

Ribozymes may also function as inhibitors of NGAL gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of NGAL mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of NGAL gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing NGAL. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In another aspect, the present invention relates to an NGAL antagonist for use in the prevention or the treatment of CKD.

In one embodiment the NGAL antagonist may consist in an antibody (the term including antibody fragment) that can block NGAL activity.

Antibodies directed against the NGAL can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against NGAL can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-NGAL single chain antibodies. NGAL antagonists useful in practicing the present invention also include anti-NGAL antibody fragments including but not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab and/or scFv expression libraries can be constructed to allow rapid identification of fragments having the desired specificity to NGAL.

Humanized anti-NGAL antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against the NGAL as above described, the skilled man in the art can easily select those blocking NGAL activity.

In another embodiment the NGAL antagonist is an aptamer directed against NGAL. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S.D., 1999. Peptide aptamers consists of a conformationally constrained antibody variable region displayed by a platform protein, such as *E. coli* Thioredoxin A that are selected from combinatorial libraries by two hybrid methods (Colas et al., 1996). Then after raising aptamers directed against the NGAL as above described, the skilled man in the art can easily select those blocking NGAL activity.

In still another embodiment, the NGAL antagonist may be a low molecular weight antagonist, e. g. a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

The inhibitor NGAL gene expression or the NGAL antagonist may be administered in the form of a pharmaceutical composition. Preferably, said inhibitor or antagonist is administered in a therapeutically effective amount.

By a "therapeutically effective amount" is meant a sufficient amount of the NGAL antagonist or inhibitor to treat and/or to prevent chronic kidney disease (CKD) at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Pharmaceutical Compositions

The inhibitor of NGAL gene expression or the NGAL antagonist for use in the prevention or the treatment of chronic kidney disease (CKD) as defined above may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of NGAL gene expression or the NGAL antagonist of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropyl amine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of NGAL gene expression or the NGAL antagonist of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

EXAMPLE

Material & Methods

Animals: Mice used for these studies were FVB/N, C57BL/6 and C57BL/6xDBA2/F1 (B6D2F1) (Charles River), mutant jck bearing a Nek8 mutation (Jackson Laboratories), transgenic EGFR-M expressing a dominant negative isoform of EGFR under the control of kidney-specific type 1 g-glutamyl transpeptidase promoter (26) and Lcn2−/− mice (19). Lcn2−/− mice on FVB/N genetic background were obtained using a marker-assisted speed congenic strategy. Ninety-three microsatellite markers spanning each autosomal chromosome (average distance of 14.2 cM) were used to discriminate C57BL/6 and FVB/N alleles (http://www.cidr.jhmi.edu/mouse). Heterozygous C57BL/6 Lcn2+/− mice were bred with heterozygous jck mice to obtain double-homozygous transgenic Lcn2−/−/jck mice. All experiments were performed on 9-week-old females, except for jck mice that were studied 3 weeks after birth. Animals were fed ad libitum and housed at constant ambient temperature in a 12-hour light cycle. Animal procedures were approved by the Departmental Director of "Services Vétérinaires de la Prefecture de Police de Paris" and by the ethical committee of the Paris Descartes University.

Mice were subjected to 75% nephrectomy (Nx) or sham-operation (controls), as previously described (26). After surgery, mice were fed a defined diet containing 30% casein and 0.5% sodium. Several groups of mice were investigated in complementary studies. For microarray studies, 6 and 9 mice from each strain were subjected to either sham-operation or Nx, respectively. For Lcn2 time course analysis, 5-6 sham-operated and 4-8 Nx mice were studied at each time point. Transgenic studies employed EGFR-M or Lcn2−/− mice and wild-type (WT) littermates; for each group, 4-6 mice were subjected to sham-operation and 10-16 mice to nephron reduction. For iron chelation experiments, 5 sham-operated and 6 Nx mice were injected with 100 mg/kg/d Desferroxamine (DFO, Sigma) by subcutaneous osmotic mini-pumps (2004, Alzet) for 2 months. For hypoxyprobe experiments, 6 sham-operated and 6 Nx mice were injected intraperitoneally with 60 mg/kg Pimonidazole (Chemicon) 2 hours before sacrifice. Post-ischemic kidneys (2 hours renal pedicle clamping) were used as positive hypoxic controls.

Mice were sacrificed 2 months after surgery. In addition, for Lcn2 time course study, mice were also sacrificed at 4 and 6 weeks after surgery. One week before sacrifice, blood pressure was recorded in both sham-operated (n=3) and subtotally nephrectomized (n=6) awake Lcn2+/+ and Lcn2−/− mice for 2 consecutive days, using tail-cuff plethysmography and PowerLab/4SP software (AD Instruments). Urine samples were also collected using metabolic cages from 6 mice of each experimental group over the course of 24 hours. At the time of sacrifice, the kidney was removed for morphological, protein and mRNA studies.

Clinical samples: The study was conducted on 87 subjects with autosomal dominant polycystic kidney disease (ADPKD) (40 M, 47 F; mean age 52.4 years; range 24.7-79.2 years). The mean serum creatinine level of patients was 252±169.9 mmol/l and the eGFR (assessed using MDRD formula (53)) was 33±20 ml/min/1.73 m2. 76 over the 87 patients were hypertensive under treatment. The decline of renal function was evaluated retrospectively over 6 years, then patients were divided into two groups: slow progressors (eGFR decline<4.5 ml/min/1.73 m2 per year, mean=2.4±0.1, n=52) or fast progressors (eGFR decline>4.5 ml/min/1.73 m2 per year, mean=6.0±0.2, n=35).

Kidneys from patients with ADPKD (n=9), oligomeganephronia (n=11) and IgA nephropathy (n=12) were analyzed for LCN2 expression. Normal kidneys not used for transplantation or tumor-free pole of kidneys removed for carcinoma were used as controls (n=9).

This protocol was approved by the Hospital Plan for Clinical Research (PHRC) program of the French Ministry of Health. Informed consent was obtained before enrollment.

Cells: For siRNA transfection experiments, transient inactivation of Hif-1α expression in mIMCD-3 cells was obtained using siRNA SMARTpool® from Dharmacon according to manufacturer's recommendations. Cells were transfected with siRNA (100 nM) using DharmaFECT®4 siRNA Transfection Reagent (Thermo Fisher Scientific). Eight hours after transfection, cells were serum starved for 12 hours and then treated with 40 ng/mL EGF (R&D systems) in serum-deprived medium for 48 hours.

For shRNA transfections, mIMCD-3 cells were stably transfected with pSuppressor Retro vector (Imgenex) containing a shRNA for Lcn2 or a scramble oligonucleotide (Dharmacon). The Lcn2 shRNA sequence contains either the cloning nucleotides 5'-ggaaatatgcacaggtatc-3' (SEQ ID NO: 1) or 5'-gctactggatcagaacatt-3' (SEQ ID NO: 2) followed by a 9-base loop and the inverted cloning sequence. In the scramble sequence, the cloning sequence is replaced by 5'-gagcgtaccagattaaagt-3' (SEQ ID NO: 3) or 5'-gattcgaccagacatgtat-3' (SEQ ID NO: 4). Cells stably transfected were maintained in DMEM/HamF12 medium containing 10% FBS.

For EGF experiments, cells were serum-starved for 18 hours and then treated with 40 ng/mL EGF in serum-deprived medium for 24-96 hours. Cells were collected at 24 hours for Lcn2 assay and apoptosis experiments and at 24-96 hours for proliferation experiments.

cDNA microarray: RNAs were obtained from whole kidneys of 9 Nx mice from each strain using RNeasy Midi kit (Qiagen) according to the manufacturer's protocol. RNAs were reverse-transcribed and labeled with either cyanine Cy-3 or Cy-5. FVB/N Cy3-cDNAs and B6D2F1 Cy5-cDNAs (and conversely FVB/N Cy5- and B6D2F1 Cy3-cDNAs) were co-hybridized on mouse cDNA microarrays containing 5579 cDNAs including expressed sequence tags (Genopole®). Preparations of RNAs, cDNAs and hybridization were performed according to the Genopole® protocol (http://www.genopole.org/html/en/home/index.php). Six arrays were hybridized. For each array, the RNAs from 3 mice were pooled. Hybridized microarrays were scanned and images were analyzed using Genepix Pro 4.0 software by the Genopole® microarray facility.

Real-time RT-PCR: Lcn2 mRNA was detected in mouse kidneys and mIMCD-3 cells by real-time RT-PCR using an ABI PRISM 7700 Sequence Detection system (Applied Biosystems). Gapdh and Sdha were used as the normalization controls in kidneys and cells, respectively.

Renal function and morphology: For mice samples, proteinuria and blood urea nitrogen (BUN) were measured using an Olympus multiparametric analyzer (Instrumentation Laboratory), whereas serum creatinine was evaluated by high performance liquid chromatography (HPLC). For human samples, creatininuria and albuminuria were measured using a Hitachi 917 analyzer (Roche Diagnostics).

Kidneys were fixed in 4% paraformaldehyde, paraffin embedded, and 4-μm sections were stained with PAS, Masson's trichrome, H&E, picro-sirius red. Ferric iron deposits were evidenced using Prussian blue staining according to Perls reaction. The degree of glomerular and interstitial lesions was evaluated using semiquantitative score methodology as previously described (7). The degree of tubular lesions was automatically quantified using a Nikon digital camera Dx/m/1200 and Lucia software (Laboratory Imaging Ltd). Ten randomly selected microscopic fields (×200) were scored. For jck mice, all the section was automatically quantified at magnification ×100. The tubular score was expressed as the ratio between the tubular dilation surface and the total section area.

In situ hybridization: In situ hybridization was carried out on 8-μm sections of paraffin-embedded mouse kidneys using digoxigenin-labeled riboprobe corresponding to the nucleotides 80 to 641 of the mouse Lcn2 sequence (NM_008491). Riboprobe was synthesized using reagents from Roche, according to the manufacturer's instructions.

Western blot: Western blot were performed as previously described (12) using either a goat antibody to mouse Lcn2 (R&D systems) at 1:1,000 in 1% milk/TBST or a rabbit antibody to mouse Hif-1α or Hif-2α (Novus Biologicals) at 1:500 and 1:200 respectively in 5% milk/TBST followed by either a rabbit horseradish peroxidase-conjugated anti-goat antibody at 1:10,000 (Dako) or a donkey horseradish peroxidase-conjugated anti-rabbit antibody at 1:2,000 (Amersham). Mouse monoclonal α-tubulin antibody (Sigma-Aldrich) was used as control. Protein extracts from kidneys of Lcn2−/− mice were used to confirm antibody specificity.

Immunohistochemistry: For mouse samples, 4-μm sections of paraffin-embedded kidneys were incubated with a goat anti-mouse Lcn2 antibody (R&D systems) at 1:300, followed by a rabbit anti-goat biotinylated antibody (Dako) at 1:200. Biotinylated antibodies were detected using HRP-labeled streptavidin (Dako) at 1:500 and 3-3'-diamino-benzidine-tetrahydrochloride (DAB) revelation.

For colocalization experiments, Lotus Tetragonolobus Lectin (LTL) was detected using a biotinylated-LTL (Vector) at 1:50, followed by a HRP-labeled streptavidin at 1:500. For Tamm-Horsfall staining, mouse kidney sections were incubated with a goat anti-Tamm-Horsfall antibody (Biogenesis) diluted 1:200, followed by a biotinylated goat antibody (DAKO) at 1:500 and a HRP-labeled streptavidin at 1:500. For Aquaporin 2 staining, sections were incubated with a rabbit anti-aquaporin 2 antibody (SIGMA) 1:400, followed by a donkey HRP-conjugated anti-rabbit antibody (Amersham) at 1:300. Staining was revealed by DAB.

For hypoxyprobe staining, 4-μm sections of paraffin-embedded kidneys were treated with pronase 0.01%, then incubated with an anti-hypoxyprobe adducuts antibody (Chemicon) 1:200, followed by a biotinylated mouse antibody (DAKO) at 1:500, a HRP-labeled streptavidin at 1:500 and DAB revelation.

For human samples, 4-μm sections of paraffin-embedded kidneys were incubated with a goat anti-human LCN2 antibody (R&D systems) at 1:100, followed by a HRP-labeled rabbit anti-goat antibody (Dako) at 1:100 and DAB revelation.

Cell proliferation assay: Proliferative cells were detected in mouse kidney using proliferating cell nuclear antigen (PCNA) or Ki-67 immunostaining. For PCNA staining, 4-μm sections of paraffin-embedded kidneys were incubated with a mouse anti-PCNA antibody (DAKO) at 1:50, followed by a sheep HRP-conjugated anti-mouse antibody (Amersham) at 1:100. For Ki-67 staining, 4-μm kidney sections were incubated with a mouse anti-human Ki-67 (BD Pharmingen), followed by a biotinylated mouse antibody (Vector) at 1:400 and a HRP-labeled streptavidin at 1:1,000. Staining was revealed by DAB. The tubular proliferation index (PI) was calculated as the number of PCNA (or Ki-67)-positive nuclei for the total number of tubular nuclei in 10 randomly selected fields. The glomerular proliferation index was calculated as the number of glomeruli with at least one PCNA-positive nuclei for the total number of glomeruli. In vitro, proliferation was evaluated by counting the cell number or by using CellTiter 96® AQueous Cell Proliferation Reagent (Promega) according to the manufacturer's instructions.

Apoptosis assay: Apoptosis was detected in 4-μm sections of paraffin-embedded kidneys by TUNEL assay using the In Situ Cell Death Detection kit (Roche) according to the manufacturer's protocol. The number of apoptotic cells was determined as the number of TUNEL-positive nuclei per tubule in 20 randomly selected fields. The glomerular apoptotic index was calculated as the number of glomeruli with at least one TUNEL-positive nuclei for the total number of glomeruli. In vitro, apoptotic cells were detected by DAPI staining and the apoptotic index was calculated as the number of apoptotic-positive nuclei for the total number of nuclei in 10 randomly selected fields.

Measurement of urinary LCN2: Fresh urine was collected with protease inhibitors, centrifuged at 2,000 rpm at 4° C. for 5 minutes and the supernatant was removed and stored at −80° C. LCN2 was measured using ELISA (Antibody-Shop). Specimens, standards and reagents were prepared according to manufacturer's instructions. LCN2 levels were expressed as nanograms per milligram of creatinine. All experiments were performed in duplicate.

Data analysis and statistics: Data were expressed as means±SEM. Differences between the experimental groups were evaluated using ANOVA, followed when significant ($P<0.05$) by the Tukey-Kramer test. When only two groups were compared, Mann-Whitney or Wilcoxon tests were used. The Pearson's correlation coefficient was used to test correlation between variables. For microarray experiments, results are expressed as a Log 2 of the ratio Cy5/Cy3. Genes with a false-discovery rate (FDR)<0.05 (using the Benjamini-Hochberg procedure) and a fold change (FC)>1.5 were considered significant. The statistical analysis was performed using Graph Prism Software.

Results

Gene profiling: To elucidate the molecular pathways of CKD progression, we performed unbiased profiling of gene expression in remnant kidneys of two mouse strains that react differently to nephron reduction. Using microarrays containing 5579 cDNAs, we found 70 genes whose expression levels differed significantly two months after nephron reduction ($P<0.05$). Among these transcripts, 44 were up-regulated and 26 were down-regulated in damaged FVB/N kidneys as compared with well-preserved kidneys from B6D2F1. Grouping these results by gene ontology category, we observed a range of functions for the 70 transcripts, although many of the down-regulated mRNA (38%) regulated metabolic processes. The gene undergoing maximal transcriptional induction (9.95 fold-change, $P=0.008$) in the FVB/N lesion-prone strain was Lipocalin 2 (Lcn2 or neutrophil gelatinase-associated lipocalin, NGAL; also known as siderocalin, 24p3 or uterocalin).

Lcn2 correlates with lesion progression in mouse and human with CKD: Lcn2 is a member of the lipocalin superfamily (13), a family of proteins that transport hydrophobic molecules such as retinoids, fatty acids and organic chelators of iron (14). Real-time RT-PCR confirmed that Lcn2 mRNA increased 10-fold two months after nephron reduction in FVB/N but not in B6D2F1 mice, while it was almost undetectable in control animals. In situ hybridization and immunohistochemistry corroborated these observations and showed a marked increase of Lcn2 mRNA and protein in damaged kidneys of FVB/N mice. Lcn2 was predominantly found in proximal tubules and in a few ascending limbs of Henle's loops and collecting ducts. High magnification revealed that Lcn2 was mainly located in cytoplasmic granules at the subapical zone. By combining in situ hybridization and immunohistochemistry on serial sections, we found that a proportion of Lcn2 must have derived from the glomerular filtrate since in some proximal tubules Lcn2 mRNA was negative while anti-Lcn2 staining was markedly positive (in situ− and antibody+). On the other hand, the majority of proximal epithelia that had undergone dilation and cystic transformation displayed both Lcn2 message and antibody staining (in situ+ and antibody+), indicating not only endocytosis of filtered protein but ongoing local synthesis and secretion of Lcn2. Renal Lcn2 mRNA and protein levels correlated with the intensity of tubular damage ($r=0.87$, $P<0.001$ and $r=0.74$, $P<0.01$, for mRNA and protein, respectively). In addition, we observed that renal Lcn2 protein content significantly correlated with Lcn2 excretion ($r=0.99$, $P<0.01$), implicating the kidney as the major source of urinary Lcn2.

A careful time course analysis of Lcn2 expression and renal morphology revealed that the increase of both Lcn2 mRNA and protein levels preceded the development of renal lesions 4 weeks after nephron reduction. Moreover, we confirmed that Lcn2 upregulation was associated with the progressive development of tubular dilations in another experimental model of CKD, the jck (juvenile cystic kidney) mice. Of note, these mice develop a form of polycystic kidney disease similar to the human autosomal dominant polycystic kidney disease (ADPKD) (15). Lastly, in patients with ADPKD who are similar to our model in displaying severe and progressive tubular dilations, LCN2 immunoreactivity was markedly increased, particularly in cysts. Urinary LCN2 was most prominent in fast progressors towards ESRF rather than in slow progressors (496±146 versus 152±52 ng/mg creatinine, $P<0.01$) and it inversely correlated with residual eGFR ($r=-0.77$, $P<0.0001$) and microalbuminuria ($r=0.72$, $P<0.0001$). Interestingly, LCN2 expression was also increased in renal tubules of kidneys from patients with either congenital nephron deficit, a pathological condition very close to nephron reduction, or IgA nephropathy, the most common primary form of CKD. Our findings in mice and humans together with recent works (16-18) suggested that Lcn2 might participate in the pathogenesis of cysts and CKD.

Lcn2 gene inactivation prevents lesion development and cyst formation: To determine the role of Lcn2 in progressive CKD, we performed 75% nephron reduction (Nx) in Lcn2$^{-/-}$ (19). To this end, we first introduced the Lcn2 mutated allele in the lesion-prone (FVB/N) background. The Lcn2$^{-/-}$ FVB/N mice reproduced normally and had no apparent phenotype under physiological conditions (data not shown). As expected, two months after nephron reduction, wild-type mice developed severe renal lesions, mainly comprising glomerulosclerosis, tubular atrophy and cystic dilation, mild interstitial fibrosis and multifocal mononuclear cell infiltration. However, the frequency and severity of renal lesions were dramatically reduced in Lcn2$^{-/-}$ mice. Quantification showed that Lcn2$^{-/-}$ mice had considerably fewer glomerular, tubular and interstitial lesions as compared with wild-type littermates. Notably, there were less tubular dilations and no cysts in Lcn2$^{-/-}$ mice. Consistently, renal function was better preserved in Lcn2$^{-/-}$ mice as compared to wild-type littermates, two months after nephron reduction. Serum creatinine and blood urea nitrogen were 5±0.5, 18±2.6 and 11±0.6 μmol/l ($P<0.01$) and 29±1, 109±15 and 65±4 mg/dl ($P<0.01$) in control, Nx Lcn2$^{-/-}$ and Nx Lcn2$^{-/31}$, respectively. As expected, mean arterial blood pressure significantly increased in wild-type mice as compared to control animals (135±7.5 and 116±3.4 mm Hg, $P<0.05$) two months after nephron reduction. The increase was of same magnitude in Lcn2$^{-/-}$ mice (143±2.2 mm Hg). Development of renal lesions was accompanied by severe proteinuria in wild-type mice (6.16±1.21 versus 0.003±0.001 mg/day, in Nx and control mice, respectively, $P<0.001$), whereas proteinuria was substantially decreased in Lcn2$^{-/-}$ animals (3.30±1.03 mg/day, $P<0.05$). Of note, Lcn2 inactivation did not change the course of nephron reduction in lesion-resistant C57BL/6 mice.

To confirm the beneficial effect of Lcn2 gene inactivation in renal deterioration and cyst formation, we bred Lcn2$^{-/-}$ mice with the jck mice. Notably, the severity of renal lesions was substantially reduced in double mutant jck/Lcn2$^{-/-}$ mice. Quantification showed that the score of tubular dilation was significantly lower in double mutant mice as compared to jck littermates three weeks after birth. Collectively, these results demonstrated that Lcn2 is an effector of renal damage during CKD progression.

Iron accumulation does not account for progressive renal dysfunction: We next aimed at elucidating the mechanisms underlying the lesion promoting effect of Lcn2. Lcn2 might act through iron mobilization (20). In fact, abnormal levels of iron accumulate in kidneys during CKD, where it may participate in the deterioration process (21, 22). Pens staining confirmed that iron content increased in damaged tubules two months after nephron reduction. However, iron accumulation was similar in remnant kidneys of Lcn2$^{-/-}$ mice as compared with wild-type littermates. More importantly, chelation of iron by desferroxamine (DFO) unexpectedly worsened renal disease in FVB/N mice. In particular, tubular dilations were more severe and diffuse in mice treated with DFO two months after nephron reduction. Notably, Lcn2 mRNA and protein expression were dramatically increased in kidneys of DFO-treated animals as compared with vehicle-treated counterparts. Proliferation of tubular cells was also significantly enhanced two months after nephron reduction in DFO-treated mice. Hence, whereas iron deposited in the proximal tubules does not account for renal deterioration in our model, the experiments with DFO clearly show that manipulating Lcn2 levels is tightly correlated with hyperproliferation and progressive damage.

Lcn2 is a target of EGFR signaling: It is known that cell proliferation contributes to the development of renal lesions, and particularly to cystogenesis (23). Previous studies have suggested that Lcn2 can be induced by a number of growth factors that stimulate tubular cell proliferation (24). Among these, Epidermal Growth Factor Receptor (EGFR) is of particular interest, since it is critical in the evolution of CKD (25). We therefore hypothesized that Lcn2 could act downstream of EGFR and mediate its growth effects. To investigate this hypothesis, we first treated renal tubular mIMCD-3 cells with EGF. Western blot analysis revealed that Lcn2 protein levels were markedly increased after addition of EGF. Quantitative RT-PCR showed that Lcn2 mRNA levels paralleled the increase of the protein in EGF-treated cells, indicating that Lcn2 gene is transcriptionally regulated by EGFR. To validate these findings in vivo, we took advantage of a line of transgenic mice that overexpresses a dominant negative EGFR isoform (EGFR-M) selectively in proximal tubular cells (26). Inhibition of EGFR prevented the increase of Lcn2 mRNA in remnant kidneys of transgenic mice, two months after nephron reduction. Consistently, the severity of renal lesions was substantially reduced in EGFR-M mice as compared with wild-type littermates.

Hif-1α is a critical intermediate between EGFR and Lcn2: We next tried to identify the factors that account for Lcn2 transcription upon EGFR activation. The observation that DFO dramatically stimulated Lcn2 expression after nephron reduction suggested that hypoxia inducible factors (HIF) might play a role. In fact, by inhibiting $Fe^{2-}$-dependent prolyl hydroxylases, DFO stabilizes Hif-1α and Hif-2α (27). Interestingly, our results showed that Hif-1α protein levels increased in damaged kidneys of FVB/N mice two months after nephron reduction. Since previous studies have shown that hypoxia may develop in damaged kidneys in CKD (28), we analyzed renal oxygenation two months after nephron reduction. Pimonidazole hypoxia probe failed to detect any positive tubules in remnant kidneys of FVB/N mice, with the exception of those located in the surgical scars, demonstrating that hypoxia did not account for Hif-1α overexpression in our experimental model of CKD. In vitro experiments confirmed that EGF stimulated Hif-1α expression in renal mIMCD-3 cells. In fact, Hif-1α protein levels markedly increased upon EGF stimulation. Hif-1α mRNA levels, determined by real time RT-PCR, changed neither in vivo after nephron reduction nor, in vitro upon EGF treatment (data not shown), suggesting that Hif-1α is induced via a post-transcriptional mechanism. In addition, we observed that the increase of Hif-1α was specific, since the expression of Hif-2α changed neither in remnant kidneys, nor in EGF-stimulated cells. More importantly, we showed that Hif-1α silencing by siRNA partially inhibited Lcn2 expression either in basal condition and, mainly, upon EGF stimulation in mIMCD-3 cell lines, indicating that Hif-1α is a critical intermediate in EGFR-induced Lcn2 overexpression.

Lcn2 mediates the proliferative effect of EGFR: To next investigate if Lcn2 mediated the mitogenic effect of EGFR, we established mIMCD-3 cell lines expressing Lcn2 shRNAs. Quantitative RT-PCR and western blots revealed that Lcn2 mRNA was depleted by 96% whereas the protein was undetectable in Lcn2-silenced cells. Interestingly, Lcn2 silencing completely abolished cell proliferation after the addition of EGF at different experimental time points. Similar results were obtained by using different clones and a second shRNA targeting Lcn2 (data not shown). We found consistent results in our mouse model in vivo. In fact, Lcn2 gene deletion prevented the increase of tubular cell proliferation two months after nephron reduction, as reflected in significantly lower PCNA-positive tubular cells in remnant kidneys of Lcn2$^{-/-}$ mice as compared with wild-type littermates. Notably, Lcn2 gene inactivation did not inhibit the increase of cell proliferation in glomeruli. These results were confirmed using an antibody directed against Ki-67, a protein selectively expressed in proliferating cells. Thus, it appears that Lcn2 is an essential mediator of the mitogenic effect of EGF in renal tubular cells.

The dual effect of Lcn2 inactivation on apoptosis: Tubular growth reflects the balance between cell proliferation and cell loss by apoptosis. Both EGFR and Lcn2 have been implicated in the control of apoptosis (25, 29). TUNEL analysis revealed an increase of apoptosis in both tubules and glomeruli of wild-type mice as compared with control animals two months after nephron reduction. The number of TUNEL-positive cells was significantly reduced in mice in both glomerular and tubular structures. However, Lcn2 silencing did not significantly affect the number of apoptotic tubular mIMCD-3 cells, regardless of the presence of EGF.

Discussion:

Unbiased profiling analyses offer a powerful approach to uncover critical mediators and dissect novel molecular networks of complex biological processes such as CKD progression. By combining experimental models of CKD, mice from different genetic backgrounds with microarray analyses, we have established a pivotal role for Lcn2 in regulating the progression of CKD and cyst formation. Furthermore, we have defined an important pathophysiological mechanism by which Lcn2 mediates the mitogenic effect of EGFR, consistent with its role in cell proliferation in cystogenesis. Inhibition of this pathway by Lcn2 gene inactivation or by the expression of a dominant negative EGFR isoform prevented lesion development in the transgenic mice. Conversely, overexpression of Lcn2 significantly correlated with hyperproliferation and CKD progression in both mice and humans. We have further identified Hif-1α as a crucial intermediate between EGFR and Lcn2-upregulation. Collectively, these results elucidate a novel molecular pathway of CKD progression and show that Lcn2 acts as a growth-promoting factor whose overexpression identifies patients with rapid CKD progression.

Lcn2, like all members of the lipocalin superfamily, binds hydrophobic ligands; the ligand is thought to define the function of the protein. Lcn2 binds enterochelin (20), parabactin (20) and carboxymycobactin (30), which are siderophores produced by bacteria for the purpose of binding iron. The siderophore-chelating property of Lcn2 renders it a bacteriostatic agent (20). Consistently, Lcn2 mutant mice have a profound defect in the defense against *E. coli* (19, 31) and *M. tuberculosis* (32). Nonetheless, Lcn2 expression dramatically increases in several aseptic pathological conditions such as cancers (33), inflammatory diseases (34) or acute kidney injury (24), suggesting that Lcn2 may have other functions. To date, its non-infectious activities have focused on its effects on cell proliferation and/or apoptosis (24), but proof of these in a physiological setting in vivo has been lacking. Even in the case of acute kidney injury, a disease which is related to CKD, it remains unclear whether Lcn2 is a critical mediator of tubular changes (19). Hence, our work is the first clear demonstration that in vivo Lcn2 has a critical function in a pathological condition other than infection, namely serving as a growth regulator which mediates CKD progression. Our findings in mice and humans may be generally applicable to many forms of CKD, because Lcn2 is also expressed in obstructive uropathy (16), diabetic nephropathy (16), and in damaged kidneys of patients with IgA nephropathy (17) or HIV-associated nephropathy (18).

Our study shows that Lcn2, which is induced by EGFR, controls aberrant growth of renal tubules and cysts. Notably, we demonstrated that Lcn2 gene inactivation inhibited proliferation of tubular cells which led to a marked decrease of cyst formation in mice. Consistently, we identified cystic tubular epithelia as the major source of Lcn2 production. These data suggest that Lcn2 might act as a tubulogenic factor that controls cell growth. This is supported by additional evidence: first, Lcn2 induced tubular development in in vitro assays in the rat (35); second, Lcn2 infusion favored tubular regeneration after ischemic injury in mice (36); third, high Lcn2 levels were associated with higher cystic growth in humans (37). This property was not limited to mammalian cells: Lpr-1, a newly identified lipocalin family member, controlled unicellular tube development in the excretory system of *Caenorhabditis Elegans* (38). Our data also suggest that Lcn2 may modulate tubular shape by controlling both cell proliferation and apoptosis. In fact, the beneficial effect of Lcn2 gene inactivation in mutant mice was accompanied by a decrease of tubular apoptosis, consistent with a previous observation in proximal tubule lacking Pkd1, a cystic disease-associated gene (39). However, this effect may be indirect since Lcn2 silencing in vitro did not affect the number of apoptotic tubular cells. Whether the growth promoting effect of Lcn2 results by the binding of Lcn2 to a unique receptor, thus inducing a signaling cascade, or alternatively by iron mobilization, as suggested by the DFO experiments, remains to be elucidated.

In the present study we observed that Lcn2 gene inactivation protected from glomerulosclerosis and interstitial fibrosis after nephron reduction, despite the fact that Lcn2 was expressed only by tubules. The mechanism for this observation remains unknown. It may result from the perfusion and filtration of serum Lcn2 which we found by immunostaining in the tubules. Alternatively, since injuries to tubular cells, i.e. proteinuria, result in the expression of tubular cytokines and growth factors that ultimately lead to mesangial cell proliferation and matrix synthesis (40), it is tempting to evoke a cross-talk between tubular and surrounding renal cells. Studies in transgenic mice strongly support this idea. For example, it has been observed that mice that overexpressed VEGF selectively in tubules developed interstitial fibrosis and glomerular disease (41). And, we have previously showed that the overexpression of a dominant negative isoform of EGFR in proximal tubules prevented the development of glomerular and interstitial lesions after nephron reduction (26). On the other hand, it has been shown that interstitial scarring resulted in the loss of microvessels which, in turn, impacted the adjacent unaffected glomeruli (42). It is worthy to note that the synthesis of paracrine mediators may increase in proliferating tubular cells (43). Hence, we speculate that, by inhibiting tubular cell proliferation, Lcn2 might protect glomeruli and interstitium from lesions development.

Activation of EGFR has been implicated in the evolution of CKD. Overexpression of an active EGFR form, the c-erb-B2 receptor, induces tubular hyperplasia and the development of renal cysts in transgenic mice (44). Conversely, expression of a dominant negative EGFR isoform inhibits cell proliferation leading to reduced tubular dilations after nephron reduction (26). Other genetic and pharmacological approaches have confirmed the key role of EGFR and cell proliferation in polycystic kidney diseases (45, 46), and overexpression and mislocalization of EGFR was observed in cystic epithelia of jck mice (15). On the other hand, we have previously established that EGFR acts as a central integrator of angiotensin II, a potent mediator of CKD (47). While the exact molecular networks that mediate the deleterious effect of EGFR during CKD have not been yet elucidated, our data point to Lcn2 as the crucial transcriptional target of EGFR during cyst formation and glomerulosclerosis. It is worthy to note that a very recent study showed that Lcn2 is also required for c-erb-B2 receptor signaling in breast cancer (48). In addition, our data show that Hif-$1\alpha$ is a critical intermediate between EGFR and Lcn2, consistent with the finding that Lcn2 is up-regulated in most pathological conditions characterized by hypoxia, such as ischemia or cancers (24, 33). Whether Hif-$1\alpha$ is more largely involved in the control of Lcn2 gene expression requires further investigations.

Clinical studies have suggested that urinary Lcn2 excretion might mark patients with the most severe clinical course (49), but whether Lcn2 is simply a marker of tubular damage or a key mediator of the deterioration process has been unknown. Our data now show a direct relation between Lcn2 expression and disease progression and provide the first demonstration that Lcn2 is instrumental in CKD. CKD is a progressive disease and there are many possible medical interventions over its course if the disease is recognized and treated in a timely manner. Current biomarkers of CKD progression, i.e, creatinine or albuminuria, have their limitations in this goal (50). An ideal biomarker should reflect tissue pathology, act as a critical component of disease and be easily detectable by non-invasive approaches. By showing that Lcn2 unites these characteristics, we have provided strong evidence for the use of this molecule as a candidate biomarker of CKD progression.

In conclusion, we have uncovered a novel function of Lcn2 and highlighted its crucial role in the pathogenesis of progressive CKD. This is the first demonstration in vivo that Lcn2 acts as a growth regulator by mediating the mitogenic effect of EGFR signaling. Moreover, we have identified Lcn2 as one of the key effectors of renal damage and cystogenesis and one of the most promising biomarkers of CKD progression, ready for study in large patient cohorts. We suspect that our findings will be critical in other pathological conditions that are also characterized by aberrant growth, such as cancers which demonstrate both EGFR activation and intensive Lcn2 expression (51, 52).

REFERENCES

Throughout this application, various references describe the state of the art to which this invention pertains. The disclosures of these references are hereby incorporated by reference into the present disclosure.

1. 2006. USRDS Am J Kidney Dis 47:1-286.
2. Meguid El Nahas, A., and Bello, A. K. 2005. Chronic kidney disease: the global challenge. Lancet 365:331-340.
3. http://kidney.niddk.nih.gov/kudiseases/pubs/kustats/index.htm, page 1.
4. Hostetter, T. H. 1995. Progression of renal disease and renal hypertrophy. Annu Rev Physiol 57:263-278.
5. Terzi, F., Ticozzi, C., Burtin, M., Motel, V., Beaufils, H., Laouari, D., Assael, B. M., and Kleinknecht, C. 1995. Subtotal but not unilateral nephrectomy induces hyperplasia and protooncogene expression. Am J Physiol 268: F793-801.
6. Kliem, V., Johnson, R. J., Alpers, C. E., Yoshimura, A., Couser, W. G., Koch, K. M., and Floege, J. 1996. Mechanisms involved in the pathogenesis of tubulointerstitial fibrosis in 5/6-nephrectomized rats. Kidney Int 49:666-678.
7. Pillebout, E., Weitzman, J. B., Burtin, M., Martino, C., Federici, P., Yaniv, M., Friedlander, G., and Terzi, F. 2003. JunD protects against chronic kidney disease by regulating paracrine mitogens. J Clin Invest 112:843-852.
8. Remuzzi, G., Benigni, A., and Remuzzi, A. 2006. Mechanisms of progression and regression of renal lesions of chronic nephropathies and diabetes. J Clin Invest 116: 288-296.
9. Esposito, C., He, C. J., Striker, G. E., Zalups, R. K., and Striker, L. J. 1999. Nature and severity of the glomerular response to nephron reduction is strain-dependent in mice. Am J Pathol 154:891-897.
10. Kren, S., and Hostetter, T. H. 1999. The course of the remnant kidney model in mice. Kidney Int 56:333-337.
11. Ma, L. J., and Fogo, A. B. 2003. Model of robust induction of glomerulosclerosis in mice: importance of genetic background. Kidney Int 64:350-355.
12. Pillebout, E., Burtin, M., Yuan, H. T., Briand, P., Woolf, A. S., Friedlander, G., and Terzi, F. 2001. Proliferation and remodeling of the peritubular microcirculation after nephron reduction: association with the progression of renal lesions. Am J Pathol 159:547-560.
13. Flower, D. R., North, A. C., and Attwood, T. K. 1991. Mouse oncogene protein 24p3 is a member of the lipocalin protein family. Biochem Biophys Res Commun 180: 69-74.
14. Schlehuber, S., and Skerra, A. 2005. Lipocalins in drug discovery: from natural ligand-binding proteins to "anticalins". Drug Discov Today 10:23-33.
15. Smith, L. A., Bukanov, N. O., Husson, H., Russo, R. J., Barry, T. C., Taylor, A. L., Beier, D. R., and Ibraghimov-Beskrovnaya, O. 2006. Development of polycystic kidney disease in juvenile cystic kidney mice: insights into pathogenesis, ciliary abnormalities, and common features with human disease. J Am Soc Nephrol 17:2821-2831.
16. Kuwabara, T., Mori, K., Mukoyama, M., Kasahara, M., Yokoi, H., Saito, Y., Yoshioka, T., Ogawa, Y., Imamaki, H., Kusakabe, T., et al. 2009. Urinary neutrophil gelatinase-associated lipocalin levels reflect damage to glomeruli, proximal tubules, and distal nephrons. Kidney Int 75:285-294.
17. Ding, H., He, Y., Li, K., Yang, J., Li, X., Lu, R., and Gao, W. 2007. Urinary neutrophil gelatinase-associated lipocalin (NGAL) is an early biomarker for renal tubulointerstitial injury in IgA nephropathy. Clin Immunol 123:227-234.
18. Paragas, N., Nickolas, T. L., Wyatt, C., Forster, C. S., Sise, M., Morgello, S., Jagla, B., Buchen, C., Stella, P., Sanna-Cherchi, S., et al. 2009. Urinary NGAL marks cystic disease in HIV-associated nephropathy. J Am Soc Nephrol 20:1687-1692.
19. Berger, T., Togawa, A., Duncan, G. S., Elia, A. J., You-Ten, A., Wakeham, A., Fong, H. E., Cheung, C. C., and Mak, T. W. 2006. Lipocalin 2-deficient mice exhibit increased sensitivity to Escherichia coli infection but not to ischemia-reperfusion injury. Proc Natl Acad Sci USA 103:1834-1839.
20. Goetz, D. H., Holmes, M. A., Borregaard, N., Bluhm, M. E., Raymond, K. N., and Strong, R. K. 2002. The neutrophil lipocalin NGAL is a bacteriostatic agent that interferes with siderophore-mediated iron acquisition. Mol Cell 10:1033-1043.
21. Nankivell, B. J., Boadle, R. A., and Harris, D. C. 1992. Iron accumulation in human chronic renal disease. Am J Kidney Dis 20:580-584.
22. Harris, D. C., Tay, Y. C., Chen, J., Chen, L., and Nankivell, B. J. 1995. Mechanisms of iron-induced proximal tubule injury in rat remnant kidney. Am J Physiol 269:F218-224.
23. Igarashi, P., and Somlo, S. 2002. Genetics and pathogenesis of polycystic kidney disease. J Am Soc Nephrol 13:2384-2398.
24. Schmidt-Ott, K. M., Mori, K., Li, J. Y., Kalandadze, A., Cohen, D. J., Devarajan, P., and Barasch, J. 2007. Dual action of neutrophil gelatinase-associated lipocalin. J Am Soc Nephrol 18:407-413.
25. Zeng, F., Singh, A. B., and Harris, R. C. 2009. The role of the EGF family of ligands and receptors in renal development, physiology and pathophysiology. Exp Cell Res 315:602-610.
26. Terzi, F., Burtin, M., Hekmati, M., Federici, P., Grimber, G., Briand, P., and Friedlander, G. 2000. Targeted expression of a dominant-negative EGF-R in the kidney reduces tubulo-interstitial lesions after renal injury. J Clin Invest 106:225-234.
27. Semenza, G. L. 2003. Targeting HIF-1 for cancer therapy. Nat Rev Cancer 3:721-732.
28. Gunaratnam, L., and Bonventre, J. V. 2009. HIF in kidney disease and development. J Am Soc Nephrol 20:1877-1887.
29. Devireddy, L. R., Gazin, C., Zhu, X., and Green, M. R. 2005. A cell-surface receptor for lipocalin 24p3 selectively mediates apoptosis and iron uptake. Cell 123:1293-1305.
30. Holmes, M. A., Paulsene, W., Jide, X., Ratledge, C., and Strong, R. K. 2005. Siderocalin (Lcn 2) also binds carboxymycobactins, potentially defending against mycobacterial infections through iron sequestration. Structure 13:29-41.
31. Flo, T. H., Smith, K. D., Sato, S., Rodriguez, D. J., Holmes, M. A., Strong, R. K., Akira, S., and Aderem, A. 2004. Lipocalin 2 mediates an innate immune response to bacterial infection by sequestrating iron. Nature 432:917-921.

32. Saiga, H., Nishimura, J., Kuwata, H., Okuyama, M., Matsumoto, S., Sato, S., Matsumoto, M., Akira, S., Yoshikai, Y., Honda, K., et al. 2008. Lipocalin 2-dependent inhibition of mycobacterial growth in alveolar epithelium. *J Immunol* 181:8521-8527.

33. Yang, J., and Moses, M. A. 2009. Lipocalin 2: a multifaceted modulator of human cancer. *Cell Cycle* 8:2347-2352.

34. Borregaard, N., and Cowland, J. B. 2006. Neutrophil gelatinase-associated lipocalin, a siderophore-binding eukaryotic protein. *Biometals* 19:211-215.

35. Yang, J., Goetz, D., Li, J. Y., Wang, W., Mori, K., Setlik, D., Du, T., Erdjument-Bromage, H.; Tempst, P., Strong, R., et al. 2002. An iron delivery pathway mediated by a lipocalin. *Mol Cell* 10:1045-1056.

36. Mori, K., Lee, H. T., Rapoport, D., Drexler, I. R., Foster, K., Yang, J., Schmidt-Ott, K. M., Chen, X., Li, J. Y., Weiss, S., et al. 2005. Endocytic delivery of lipocalin-siderophore-iron complex rescues the kidney from ischemia-reperfusion injury. *J Clin Invest* 115:610-621.

37. Bolignano, D., Coppolino, G., Campo, S., Aloisi, C., Nicocia, G., Frisina, N., and Buemi, M. 2007. Neutrophil gelatinase-associated lipocalin in patients with autosomal-dominant polycystic kidney disease. *Am J Nephrol* 27:373-378.

38. Stone, C. E., Hall, D. H., and Sundaram, M. V. 2009. Lipocalin signaling controls unicellular tube development in the *Caenorhabditis elegans* excretory system. *Dev Biol* 329:201-211.

39. Wei, F., Karihaloo, A., Yu, Z., Marlier, A., Seth, P., Shibazaki, S., Wang, T., Sukhatme, V. P., Somlo, S., and Cantley, L. G. 2008. Neutrophil gelatinase-associated lipocalin suppresses cyst growth by Pkd1 null cells in vitro and in vivo. *Kidney Int* 74:1310-1318.

40. Tang, S., Leung, J. C., Tsang, A. W., Lan, H. Y., Chan, T. M., and Lai, K. N. 2002. Transferrin up-regulates chemokine synthesis by human proximal tubular epithelial cells: implication on mechanism of tubuloglomerular communication in glomerulopathic proteinuria. *Kidney Int* 61:1655-1665.

41. Hakroush, S., Moeller, M. J., Theilig, F., Kaissling, B., Sijmonsma, T. P., Jugold, M., Akeson, A. L., Traykova-Brauch, M., Hosser, H., Hahnel, B., et al. 2009. Effects of increased renal tubular vascular endothelial growth factor (VEGF) on fibrosis, cyst formation, and glomerular disease. *Am J Pathol* 175:1883-1895.

42. Fine, L. G., and Norman, J. T. 2008. Chronic hypoxia as a mechanism of progression of chronic kidney diseases: from hypothesis to novel therapeutics. *Kidney Int* 74:867-872.

43. Strutz, F., Zeisberg, M., Hemmerlein, B., Sattler, B., Hummel, K., Becker, V., and Muller, G. A. 2000. Basic fibroblast growth factor expression is increased in human renal fibrogenesis and may mediate autocrine fibroblast proliferation. *Kidney Int* 57:1521-1538.

44. Stocklin, E., Botteri, F., and Groner, B. 1993. An activated allele of the c-erbB-2 oncogene impairs kidney and lung function and causes early death of transgenic mice. *J Cell Biol* 122:199-208.

45. Richards, W. G., Sweeney, W. E., Yoder, B. K., Wilkinson, J. E., Woychik, R. P., and Avner, E. D. 1998. Epidermal growth factor receptor activity mediates renal cyst formation in polycystic kidney disease. *J Clin Invest* 101:935-939.

46. Sweeney, W. E., Chen, Y., Nakanishi, K., Frost, P., and Avner, E. D. 2000. Treatment of polycystic kidney disease with a novel tyrosine kinase inhibitor. *Kidney Int* 57:33-40.

47. Lautrette, A., Li, S., Alili, R., Sunnarborg, S. W., Burtin, M., Lee, D. C., Friedlander, G., and Terzi, F. 2005. Angiotensin II and EGF receptor cross-talk in chronic kidney diseases: a new therapeutic approach. *Nat Med* 11:867-874.

48. Leng, X., Ding, T., Lin, H., Wang, Y., Hu, L., Hu, J., Feig, B., Zhang, W., Pusztai, L., Symmans, W. F., et al. 2009. Inhibition of lipocalin 2 impairs breast tumorigenesis and metastasis. *Cancer Res* 69:8579-8584.

49. Nickolas, T. L., Barasch, J., and Devarajan, P. 2008. Biomarkers in acute and chronic kidney disease. *Curr Opin Nephrol Hypertens* 17:127-132.

50. Lemley, K. V. 2007. An introduction to biomarkers: applications to chronic kidney disease. *Pediatric Nephrol* 22:1849-1859.

51. Shepard, H. M., Brdlik, C. M., and Schreiber, H. 2008. Signal integration: a framework for understanding the efficacy of therapeutics targeting the human EGFR family. *J Clin Invest* 118:3574-3581.

52. Devarajan, P. 2007. Neutrophil gelatinase-associated lipocalin: new paths for an old shuttle. *Cancer Ther* 5:463-470.

53. Levey, A. S., Bosch, J. P., Lewis, J. B., Greene, T., Rogers, N., and Roth, D. 1999. A more accurate method to estimate glomerular filtration rate from serum creatinine: a new prediction equation. Modification of Diet in Renal Disease Study Group. *Ann Intern Med* 130:461-470.

The invention claimed is:

1. A method of treating chronic kidney disease (CKD) in a patient in need thereof, comprising
   administering to said patient an inhibitor of Neutrophil Gelatinase-Associated Lipocalin (NGAL) gene expression, wherein said inhibitor is antisense RNA.

2. The method according to claim 1, wherein the CKD is selected in the group consisting of polycystic kidney disease, glomerulonephritis, interstitial nephritis, nephropathy and obstructive uropathy.

3. The method of claim 2, wherein said polycystic kidney disease is Autosomal Dominant Polycystic Kidney Disease (ADPKD) or Autosomal Recessive Polycystic Kidney Disease (ARPKD).

4. The method of claim 1, wherein said inhibitor is shRNA.

5. The method of claim 4, wherein the shRNA has a sequence selected from SEQ ID NO: 1 or SEQ ID NO: 2.

* * * * *